(12) United States Patent
Toyota et al.

(10) Patent No.: US 11,453,786 B2
(45) Date of Patent: Sep. 27, 2022

(54) DIALKYLZINC- AND DIALKYLZINC PARTIAL HYDROLYSATE-CONTAINING SOLUTION, AND METHOD FOR PRODUCING ZINC OXIDE THIN FILM USING SOLUTION

(71) Applicant: Tosoh Finechem Corporation, Shunan (JP)

(72) Inventors: Kouji Toyota, Shunan (JP); Kenichi Haga, Shunan (JP)

(73) Assignee: TOSOH FINECHEM CORPORATION, Shunan (JP)

( * ) Notice: Subject to any disclaimer, the term of this patent is extended or adjusted under 35 U.S.C. 154(b) by 297 days.

(21) Appl. No.: 16/481,104

(22) PCT Filed: Jan. 30, 2018

(86) PCT No.: PCT/JP2018/002862
§ 371 (c)(1),
(2) Date: Jul. 26, 2019

(87) PCT Pub. No.: WO2018/143156
PCT Pub. Date: Aug. 9, 2018

(65) Prior Publication Data
US 2021/0009813 A1    Jan. 14, 2021

(30) Foreign Application Priority Data

Feb. 2, 2017  (JP) .............................. JP2017-017300

(51) Int. Cl.
*C09D 1/00*       (2006.01)
*C09D 7/20*       (2018.01)
(Continued)

(52) U.S. Cl.
CPC ............... *C09D 1/00* (2013.01); *C01G 9/02* (2013.01); *C09D 7/20* (2018.01); *C23C 18/1216* (2013.01); *H01B 1/02* (2013.01); *H01B 13/30* (2013.01)

(58) Field of Classification Search
CPC ...................................... C09D 1/00
See application file for complete search history.

(56) References Cited

FOREIGN PATENT DOCUMENTS

| CN | 103153865 A | 6/2013 |
|----|-------------|--------|
| JP | H07182939 A | 7/1995 |

(Continued)

OTHER PUBLICATIONS

Office Action dated Jan. 27, 2021 in TW Application No. 107103770.

(Continued)

*Primary Examiner* — William D Young
(74) *Attorney, Agent, or Firm* — Panitch Schwarze Belisario & Nadel LLP

(57) ABSTRACT

A solution containing a diketone compound having an alkoxy group, a dialkylzinc represented by general formula (1) and/or a partial hydrolysate of the dialkylzinc, and a solvent is described. A method for producing a zinc oxide thin film involves applying the dialkylzinc solution or a solution containing a dialkylzinc partial hydrolysate to a base material.

$$ZnR^{10}_2 \quad (1)$$

In the formula, $R^{10}$ is a $C_{1-6}$ linear or branched alkyl group. The solution containing dialkylzinc or dialkylzinc partial hydrolysate can be handled in air, making it possible to form a transparent thin film having high adhesiveness to a substrate even with film formation in air.

13 Claims, 2 Drawing Sheets

(51) Int. Cl.
*C01G 9/02* (2006.01)
*C23C 18/12* (2006.01)
*H01B 1/02* (2006.01)
*H01B 13/30* (2006.01)

(56) References Cited

FOREIGN PATENT DOCUMENTS

| | | | |
|---|---|---|---|
| JP | H1152600 A | 2/1999 | |
| JP | 2005350423 A | 12/2005 | |
| JP | 2006342960 A | 12/2006 | |
| JP | 2008013653 A | 1/2008 | |
| JP | 2008088511 A | 4/2008 | |
| JP | 2008120686 A | 5/2008 | |
| JP | 2009120873 A | 6/2009 | |
| JP | 2010254481 A | 11/2010 | |
| JP | 2011168407 A | 9/2011 | |
| JP | 2011170979 A | 9/2011 | |
| JP | 2012087019 A | 5/2012 | |
| JP | 2012184192 A | 9/2012 | |
| JP | 2016216292 A | 12/2016 | |
| WO | 2008041444 A1 | 4/2008 | |
| WO | 2012053542 A1 | 4/2012 | |
| WO | 2012120918 A1 | 9/2012 | |

OTHER PUBLICATIONS

Office Action dated Jul. 28, 2020 in JP Application No. 2017017300 (with English Machine Translation).
International Preliminary Report on Patentability dated Aug. 6, 2019 in International Application No. PCT/JP2018/002862.
International Search Report dated Apr. 24, 2018 in International Application No. PCT/JP2018/002862.
Extended European Search Report dated Nov. 16, 2020 in EP Application No. 18747943.1.
Office Action dated Jan. 5, 2021 in JP Application No. 2017017300.
Office Action dated Nov. 25, 2020 in IN Application No. 201917031094.
Office Action dated May 25, 2021 in JP Application No. 2017017300 (with English Machine Translation).
Office Action dated Jun. 24, 2021 in CN Application No. 201880009707.5 (with English Machine Translation).
Manzi et al., "Aerosol-Assisted Chemical-Vapour Deposition of Zinc Oxide from Single-Source Beta-Iminoesterate Precursors," European Journal of Inorganic Chemistry, vol. 22, pp. 3658-3665 (2015) (Abstract Only).
Office Action dated Apr. 2, 2022 in CN Application No. 201880009707.5.
Office Action dated Jul. 14, 2022 in KR Application No. 1020197023428 (with English Machine Translation).

DIALKYLZINC- AND DIALKYLZINC PARTIAL HYDROLYSATE-CONTAINING SOLUTION, AND METHOD FOR PRODUCING ZINC OXIDE THIN FILM USING SOLUTION

CROSS REFERENCE TO RELATED APPLICATION

This application is a Section 371 of International Application No. PCT/JP2018/002862, filed Jan. 30, 2018, which was published in the Japanese language on Aug. 9, 2018, under International Publication No. WO 2018/143156 A1, which claims priority under 35 U.S.C. § 119(b) to Japanese Application No. 2017-017300 filed Feb. 2, 2017, the disclosures of which are incorporated herein by reference in their entirety.

TECHNICAL FIELD

The present invention relates to a solution containing at least one of a dialkylzinc and a dialkylzinc partial hydrolysate, and to a method for producing a zinc oxide thin film using the solution.

BACKGROUND ART

Transparent zinc oxide thin films having high transparency to visible light are used in a broad range of applications, such as photocatalyst films, UV cutting films, infrared reflective films, CIGS, buffer layers of organic thin-film solar cells, electrode films of dye-sensitized solar cells, antistatic films, thin-film transistors, compound semiconductor light-emitting elements, phosphor elements, antibacterial/deodorant films, piezoelectric films, varistor films and plating films (NPL 1).

Although various methods are known as methods for producing transparent zinc oxide thin films (NPL 2), production by coating, which uses simple equipment and requires no vacuum vessels, and boasts high productivity and low film production costs on account of the high film formation rates, is preferred.

Coating methods include for instance spin coating (PTL 1), dip coating (NPL 3) and spray pyrolysis (NPL 4).

A zinc oxide thin film is obtained herein through heating a substrate to a temperature of 350° C. or higher after coating by spin coating, dip coating or spray pyrolysis.

Plastic substrates have come to be used as substrates of transparent zinc oxide thin films. Accordingly, heating during formation of a transparent zinc oxide thin film must be carried out at or below the heat resistance temperature of a plastic substrate. In the above spin coating, dip coating or spray pyrolysis methods, however, it is not possible to obtain a transparent zinc oxide thin film through heating at or below the heat resistance temperature of a plastic.

Therefore, studies by the inventors led to the finding of a method for forming a transparent zinc oxide thin film even at a temperature of 300° C. or lower by using a dialkylzinc partial hydrolysate-containing solution obtained through reaction of a dialkylzinc and water (PTL 2).

[PTL 1] Japanese Patent Application Publication No. H07-182939

[PTL 2] Japanese Patent Application Publication No. 2010.-254481

[NPL 1] "Zinc Oxide Transparent Conductive Films: Towards Next-Generation Displays" Hakusui Co., Ltd. General magazine, Info, Volume 13 (2005) p. 1

[NPL 2] Technology of Transparent Conductive Films, edited by the 166th Committee on Photonic and Electronic Oxide Materials of the Japan Society for the Promotion of Science, Second edition (Revised) (2006) pp. 165 to 173

[NPL 3] Y. Ohya et al. Mater. Sci., 29, pp. 4099 to 4103 (1994)

[NPL 4] J. Aranovich et al., J. Vac. Sci. Technol., 16 (4), pp. 994 to 1002 (1979)

PTL 1 and 2 and NPL 1 to 4 are expressly incorporated herein by reference in their entirety.

SUMMARY OF INVENTION

Technical Problem

Diethylzinc partial hydrolysate-containing solutions exhibit reactivity with water or moisture. In order to form a transparent zinc oxide thin film, therefore conventionally, the film has been ordinarily required to be produced in an inert gas, such as nitrogen or argon, supplied in a dry state resulting from removal of water or moisture, or in the air having been subjected to a drying treatment. This has been problematic in that performing operations while maintaining an inert gas or air n a dry state require an inert gas and inert gas supply equipment, or an air drying apparatus, as well as gas holding equipment such as a glove box, which renders the cost of forming zinc oxide thin films somewhat higher than in ordinary coating methods.

An object of the present invention is to provide a solution containing at least one of a dialkylzinc and a dialkylzinc partial hydrolysate, that allows forming a zinc oxide thin film in the air (the atmosphere) not having been subjected to a drying treatment. Further, the present invention provides a method for producing a zinc oxide thin film that can be carried out even in the air.

Solution to Problem

The present invention is as follows.

A solution containing a diketone compound having an alkoxy group, a dialkylzinc represented by formula (1) below and/or a partial hydrolysate of the dialkylzinc, and a solvent.

$$ZnR^{10}{}_2 \qquad (1)$$

(In the formula, $R^{10}$ is a $C_1$-$C_6$ linear or branched alkyl group.)

The solution according to [1], wherein the diketone compound having an alkoxy group is one or two or more diketone compounds selected from the group consisting of an α-diketone compound having an alkoxy group, a β-diketone compound having an alkoxy group, an α-keto ester and a β-keto ester.

The solution according to [1] or [2], wherein the diketone compound having an alkoxy group is a compound represented by formula (2) or formula (3), or a mixture thereof.

(In the formula, $R_1$ represents a substituent selected from the group consisting of $C_1$-$C_6$ alkyl groups, phenyl groups, and benzyl groups, and $R_2$ represents a $C_1$-$C_6$ alkyl group.)

(3)

(In the formula, $R_1$ represents a substituent selected from the group consisting of $C_1$-$C_6$ alkyl groups, phenyl groups and benzyl groups; $R_2$ represents a $C_1$-$C_6$ alkyl group; and $R_3$ and $R_4$ each represent hydrogen or a $C_1$-$C_6$ alkyl group.)

The solution according to any one of [1] to [3], wherein the diketone compound having an alkoxy group is methyl acetoacetate, ethyl acetoacetate, isopropyl acetoacetate, butyl acetoacetate and ethyl pyruvate, or a mixture thereof.

The solution according to any one of [1] to [4], wherein a molar ratio of the diketone compound having an alkoxy group contained in the solution to zinc in the dialkylzinc or the partial hydrolysate of the dialkylzinc 0.01 to 2.

The solution according to any one of [1] to herein the dialkylzinc is diethylzinc.

The solution according to any one of [1] to [6], wherein the partial hydrolysate of the dialkylzinc is a partial hydrolysate resulting from hydrolysis with water at a molar ratio in the range of 0.4 to 0.9 with respect to zinc in the dialkylzinc.

The solution according to any one of [1] to [7], wherein the partial hydrolysate of the dialkylzinc is a partial hydrolysate represented by formula (4) below.

$$R^{10}\text{—}Zn\text{—}[O\text{—}Zn]_m\text{—}R^{10} \quad (4)$$

(In the formula, $R^{10}$ is a $C_1$-$C_6$ linear or branched alkyl group, and m is an integer from 1 to 20.)

The solution according to any one of [1] to [8], wherein the solvent is at least one solvent selected from the group consisting of aliphatic hydrocarbons, alicyclic hydrocarbons, aromatic hydrocarbons, hydrocarbon solvents, ether compounds, ethylene glycol dialkyl ether compounds, diethylene glycol dialkyl ether compounds, triethylene glycol dialkyl ether compounds, propylene glycol dialkyl compounds, dipropylene glycol dialkyls, tripropylene glycol dialkyl compounds, linear amide compounds and cyclic amide compounds.

A method for producing a zinc oxide thin film, including a step of coating a base material with the solution according to any one of [1] to [9].

The production method according to [10], including a step of heating the base material.

The production method according to [10] or [11], wherein base material is coated with the solution in a state where the base material is heated to a temperature of 500° C. or lower.

The production method according to any one of [10] to [12], wherein the coating performed in the air.

The production method according to any one of [10] to [13], wherein the coating is performed in an atmosphere having a relative humidity of 35% to 80%.

The production method according to [10] to [14], wherein the zinc oxide thin film has a transmittance equal to or higher than 80% to visible light of 550 nm.

Advantageous Effects of Invention

The present invention succeeds in providing a solution containing at least one of a dialkyzinc and a dialkylzinc partial hydrolysate that allows forming a transparent zinc oxide thin film in the air. Further, by using the solution containing at least one of a dialkylzinc and a dialkylzinc partial hydrolysate of the present invention it is possible to form a transparent zinc oxide thin film with high adhesion to a base material, even when film formation is carried out in the air.

DESCRIPTION OF EMBODIMENTS

[Dialkylzinc-Containing Solution]

A first aspect of the present invention is a dialkylzinc-containing solution that contains a dialkylzinc represented by formula (1), and further contains a diketone compound having an alkoxy group.

$$ZnR^{10}{}_2 \quad (1)$$

(In the formula, $R^{10}$ is a $C_1$-$C_6$ linear or branched alkyl group.) Examples of the alkyl group include, although not limited to, methyl groups, ethyl groups, isopropyl groups, isobutyl groups and tert-butyl groups.

[Dialkylzinc Partial Hydrolysate-Containing Solution]

A second aspect of the present invention is a dialkylzinc partial hydrolysate-containing solution that contains a partial hydrolysate of a dialkylzinc represented by formula (1), and a solvent, and further contains a diketone compound having an alkoxy group.

The partial hydrolysate can be a partial hydrolysate resulting from hydrolysis with water at a molar ratio in the range of 0.4 to 0.9 with respect to zinc in the dialkylzinc. The partial hydrolysate is suitably a product obtained by hydrolyzing a mixture of the dialkylzinc and the solvent through addition of water; this is because the dialkylzinc partial hydrolysate-containing solution of the present invention can be obtained by a hydrolysis procedure.

$$ZnR^{10}{}_2 \quad (1)$$

(In the formula, $R^{10}$ is a $C_1$-$C_6$ linear or branched alkyl group.)

Examples of the alkyl group include, although not limited to, methyl groups, ethyl groups, isopropyl groups, isobutyl groups and tert-butyl groups.

[Dialkylzinc]

Examples of the dialkylzinc represented by formula (1) include dimethylzinc, diethylzinc, diisopropylzinc, diisobutylzinc and di-tert-butylzinc. The dialkylzinc is preferably diethylzinc because of its low cost. The dialkylzinc is, however, not meant to be limited to these compounds.

[Solution Containing at Least One of Dialkylzinc and Dialkylzinc Partial Hydrolysate]

In the present invention, the dialkylzinc solution and the dialkylzinc partial hydrolysate described above may be used each independently, or may be used in admixture with each other. In other words, a solution containing at least one of a dialkylzinc and a dialkylzinc partial hydrolysate can be used.

[Solvent]

Examples of the solvent that can be used in the solution containing at least one of a dialkylzinc and a dialkylzinc partial hydrolysate include for instance aliphatic hydrocarbons such as n-hexane, octane and n-decane; alicyclic hydrocarbons such as cyclopentane, cyclohexane, methyl cyclohexane and ethyl cyclohexane; aromatic hydrocarbons such as benzene, toluene, xylene and cumene; hydrocarbon solvents such as mineral spirit, solvent naphtha, kerosene and petroleum ether; ether compounds such as diethyl ether, tetrahydrofuran, t-butyl methyl ether, di-n-propyl ether, diisopropyl ether, 1,4-dioxane, 1,3-dioxalane, dibutyl ether, cyclopentyl methyl ether and anisole; ethylene glycol dialkyl ether compounds such as 1,2-dimethoxyethane, 1,2-diethoxyethane and 1,2-dibutoxyethane; diethylene glycol dialkyl ether compounds such as diethylene glycol dimethyl ether, diethylene glycol diethyl ether and diethylene glycol dibutyl ether; triethylene glycol dialkyl ether compounds such as triethylene glycol dimethyl ether and triethylene glycol diethyl ether; propylene glycol dialkyl compounds such as propylene glycol dimethyl ether; dipropylene glycol dialkyls such as dipropylene glycol dimethyl; tripropylene glycol dialkyl compounds such as tripropylene glycol dimethyl; linear amide compounds such as N,N-di ethylacetamide, N,N-dimethylpropionamide and hexamethylphosphoramide; and cyclic amide compounds such as N-methyl-2-pyrrolidone (also abbreviated as NMP), 1,3-dimethylimidazolidinone and 1,3-dimethyl-3,4,5,6-tetrahydro-2(1H)-pyrimidinone; as well as mixtures of the foregoing.

[Production of Dialkylzinc-Containing Solution]

The dialkylzinc-containing solution is prepared through mixing of the dialkylzinc and the solvent. Specifically, taking reactivity of the dialkylzinc into consideration, the solution is prepared for instance by dissolving the dialkylzinc in the solvent in a dry atmosphere (for instance an inert gas atmosphere supplied in a dry state).

The concentration of the dialkylzinc in the dialkylzinc-containing solution can be set to 0.1 to 50 mass %, and preferably lies in the range of 0.1 to 30 mass %, from the viewpoint of ease of film formation by coating (for instance adhesion and homogeneity of the formed film). The above ranges are however exemplary, and are not meant to be limiting.

Addition of the dialkylzinc to the solvent can be made as appropriate for instance depending on the type and volume of the materials to be mixed. For instance, the solvent is added for a period in the range of 1 minutes to 10 hours. Any temperature between −20° C. to 150° C. can be selected during addition. Preferably, the temperature lies in the range −20° C. to 80° C. taking for instance safety into consideration. The above ranges are however exemplary, and are not meant to be limiting.

After addition of the solvent, aging can be conducted as needed for 0.1 to 50 hours, in order to promote mixing of the dialkylzinc. Any temperature in the range of −20° C. to 150° C. can be selected as the aging temperature. The above ranges are however exemplary, and are not meant to be limiting.

The solvent and the dialkylzinc can be introduced into a reaction vessel in accordance with any common method. The pressure in the reaction vessel is not limited. The step of preparing a dialkylzinc-containing solution is not particularly limited, and may involve any from among a batch operation, a semi-batch operation and a continuous operation, but is preferably a batch operation.

[Production of Dialkylzinc Partial Hydrolysate-Containing Solution]

The dialkylzinc partial hydrolysate is prepared by using water or a water-containing solution in a molar ratio in the range of 0.4 to 0.9 with respect to the dialkylzinc. With a molar ratio lower than 0.4 of water with respect to the dialkylzinc, it is difficult to form a uniform zinc oxide thin film, in that the coating tends to remain in a liquid state (a solid state is not achieved readily) even after removal of the solvent by drying, More preferably, the molar ratio of water with respect to the dialkylzinc is 0.6 or higher, from the viewpoint of forming a uniform zinc oxide thin film. When on the other hand the molar ratio of water with respect to the dialkylzinc exceeds 0.9, an insoluble gel or a solid precipitates in the solvent, and it is difficult to form a uniform zinc oxide thin film out of that gel or solid. The precipitated gel or solid can be removed by filtration, but this is undesirable on account of the loss of zinc arising from doing so.

Taking reactivity of the dialkylzinc into consideration, the dialkylzinc partial hydrolysate can be prepared, in concrete terms, for instance by adding water or a water-containing solution to a solution resulting from dissolving the dialkylzinc in a solvent, in a dry atmosphere (for instance, in an inert gas atmosphere that is supplied in a dry state). Water itself (pure water not being a mixture with a solvent) may be added, but preferably a water-containing solution is added, from the viewpoint of controlling heat generation during the reaction between the dialkylzinc and water. As the solvent of the water-containing solution, among the above solvents, for instance an ether compound, an ethylene glycol dialkyl ether compound, a diethylene glycol dialkyl ether compound, a triethylene glycol dialkyl ether compound, a propylene glycol dialkyl compound, a dipropylene glycol dialkyl, a tripropylene glycol dialkyl compound, a linear amide compound or a cyclic amide compound, or a mixture of the foregoing is preferably used, from the viewpoint of the solubility of water in the solvent and ease of production.

The concentration of the dialkylzinc in the dialkylzinc solution resulting from addition of water or of a water-containing solution can be set to 0.1 to 50 mass %, and lies preferably in the range of 0.1 to 30 mass %, from the viewpoint of ease of film formation by coating (for instance adhesion and homogeneity of the formed film). The above ranges are however exemplary, and are not meant to be limiting. Addition of water or of a water-containing solution to the dialkylzinc solution can be made as appropriate for instance depending on the type and volume of the materials to be mixed. For instance, the solvent is added for a period in the range of 1 minutes to 10 hours. Any temperature between −20° C. to 150° C. can be selected during addition. Preferably, the temperature lies in the range −20° C. to 80° C. taking for instance safety into consideration. The above ranges are however exemplary, and are not meant to be limiting.

After addition of water or a water-containing solution, aging can be conducted for 0.1 to 50 hours in order to promote mixing of the dialkylzinc. Any temperature in the range of −20° C. to 150° C. can be selected as the aging temperature. The above ranges are however exemplary, and are not meant to be limiting.

The solvent, the dialkylzinc, water or the water-containing solution can be introduced into a reaction vessel in accordance with any common method. The pressure in the reaction vessel is not limited. The dialkylzinc partial hydrolysis reaction step is not particularly limited, and may involve any from among a batch operation, a semi-batch operation and a continuous operation, but is preferably a batch operation.

The dialkylzinc partial hydrolysate-containing solution is obtained as a result of the above partial hydrolysis. Compositions of partial hydrolysates have been analyzed for a long time. However, the reported results on the compositions of the products varied, and product compositions have not been clearly identified. Further, product compositions vary for instance depending on solvent, concentration, molar ratios of water added, addition temperature, reaction temperature and reaction time. It is estimated that the dialkylzinc, partial hydrolysate in the method of the present invention is a mixture of compounds containing the structural units represented by formula (4) below.

$$R^{10}-Zn-[O-Zn]_m-R^{10} \qquad (4)$$

(In the formula, $R^{10}$ is identical to $R^{10}$ in formula (1), and m is an integer from 1 to 20.)

The above partial hydrolysis is preferably carried out under conditions such that a solid (gel) or the like does not precipitate, and the solid (gel) or the like is a complete hydrolysate (zinc oxide) in an advanced stage of hydrolysis of dialkylzinc, or is a partial hydrolysate in which m in formula (4) exceeds 20, the amount of alkyl groups $R^{10}$ in the molecule is decreased, and solubility in the solvent lowers. In a case where such a solid (gel) or the like precipitates after completion of partial hydrolysis, the solid or the like can be removed by purification using a method such as filtration, centrifugation or decantation. As a result of the removal procedure, a dialkylzinc partial hydrolysate-containing solution that contains substantially only a partial hydrolysate dissolved in the solvent, and which is suitable for preparing a zinc oxide thin film having good transparency, can be obtained.

The solids concentration of the dialkylzinc partial hydrolysate-containing solution can be adjusted (increased) for instance through concentrating (solvent removal). After concentrating or without concentrating, a solvent used in the hydrolysis reaction or a solvent different from the solvent used in the hydrolysis reaction can be added to adjust the solids concentration, polarity, viscosity, boiling point, economy and so forth, as appropriate.

Examples of the solvent different from the solvent used in the hydrolysis reaction include for instance aliphatic hydrocarbons such as n-hexane, octane and n-decane; alicyclic hydrocarbons such as cyclopentane, cyclohexane, methyl cyclohexane and ethyl cyclohexane; aromatic hydrocarbons such as benzene, toluene, xylene and cumene; hydrocarbon solvents such as mineral spirit, solvent naphtha, kerosene and petroleum ether; ether compounds such as diethyl ether, tetrahydrofuran, t-butyl methyl ether, di-n-propyl ether, diisopropyl ether, 1,4-dioxane, 1,3-dioxalane, dibutyl ether, cyclopentyl methyl ether and anisole; ethylene glycol dialkyl ether compounds such as 1,2-dimethoxyethane, 1,2-diethoxyethane and 1,2-dibutoxyethane; diethylene glycol dialkyl ether compounds such as diethylene glycol dimethyl ether, diethylene glycol diethyl ether and diethylene glycol dibutyl ether; triethylene glycol dialkyl ether compounds such as triethylene glycol dimethyl ether and triethylene glycol diethyl ether; propylene glycol dialkyl compounds such as propylene glycol dimethyl ether; dipropylene glycol dialkyls such as dipropylene glycol dimethyl; tripropylene glycol dialkyl compounds such as tripropylene glycol dimethyl; linear amide compounds such as N,N-dimethylacetamide, N,N-dimethylpropionamide and hexamethylphosphoramide; and cyclic amide compounds such as N-methyl-2-pyrrolidone (also abbreviated as NMP), 1,3-dimethyl-imidazolidinone and 1,3-dimethyl-3,4,5,6-tetrahydro-2(1H)-pyrimidinone; as well as mixtures of the foregoing.

The content of the dialkylzinc partial hydrolysate in the dialkylzinc partial hydrolysate-containing solution of the present invention can be appropriately determined depending on the intended use. The content can be adjusted through adjustment of the amount of solvent that is used. The content of the dialkylzinc partial hydrolysate can be adjusted as appropriate for instance within the range of 0.1 to 50 mass % taking into consideration for example properties suited to the production of the zinc oxide thin film described below. However, the content of the dialkylzinc partial hydrolysate is not meant to be limited to the above range.

[Solution Containing Diketone Compound Having Alkoxy Group of Present Invention]

In the present invention, the solution containing at least one of a dialkylzinc and a dialkylzinc partial hydrolysate further contains a diketone compound having an alkoxy group.

In particular, specific examples of the diketone compound having an alkoxy group that can be used in the present invention include α- and β-keto esters.

Esters of α-ketonic acids used in the present invention are compounds represented by formula (2) below.

(2)

(In the formula, $R_1$ represents a substituent selected from the group consisting of $C_1$-$C_6$ alkyl groups, phenyl groups, and benzyl groups, and $R_2$ represents a $C_1$-$C_6$ alkyl group.)

Concrete examples of α-keto esters include for instance glyoxylate esters such as methyl glyoxylate, ethyl glyoxylate, n-propyl glyoxylate, isopropyl glyoxylate, n-butyl glyoxylate, n-pentyl glyoxylate and n-hexyl glyoxylate; pyruvate esters such as methyl pyruvate, ethyl pyruvate, n-propyl pyruvate, isopropyl pyruvate, n-butyl pyruvate, n-pentyl pyruvate and n-hexyl pyruvate; phenylglyoxylate esters such as methyl phenylglyoxylate, ethyl phenylglyoxylate, n-propyl phenylglyoxylate, isopropyl phenylglyoxylate, n-butyl phenylglyoxylate, n-pentyl phenylglyoxylate and n-hexyl phenylglyoxylate; and phenylpyruvate esters such as methyl phenylpyruvate, ethyl phenylpyruvate, n-propyl phenylpyruvate, i-propyl phenylpyruvate, n-butyl phenylpyruvate, n-pentyl phenylpyruvate and n-hexyl phenylpyruvate.

β-keto esters used in the present invention are compounds represented by formula (3) below.

(3)

(In the formula, $R_1$ represents a substituent selected from the group consisting of $C_1$-$C_6$ alkyl groups, phenyl groups and benzyl groups; $R_2$ represents a $C_1$-$C_6$ alkyl group; and $R_3$ an $R_4$ each represent hydrogen or a $C_1$-$C_6$ alkyl group.) Herein $R_1$ may be a $C_1$-$C_6$ alkyl group, which in turn may be linear or branched, and may be preferably a methyl group or an ethyl group. Further, $R_2$ may be a $C_1$-$C_6$ alkyl group, which in turn may be linear or branched, and may be preferably a methyl group or an ethyl group.

Concrete examples of β-keto esters include for instance acetoacetate esters such as methyl acetoacetate, ethyl acetoacetate, n-propyl acetoacetate, isopropyl acetoacetate, n-butyl acetoacetate, sec-butyl acetoacetate and t-butyl acetoacetate; propionylacetate esters such as methyl propionylacetate, ethyl propionylacetate, propyl propionylacetate, isopropyl propionylacetate, butyl propionylacetate, isobutyl propionylacetate, amyl propionylacetate and isoamyl propionylacetate; as well as ethyl butyrylacetate, ethyl isobutyrylacetate, ethyl valerylacetate, ethyl isovalerylacetate, ethyl pivaloylacetate, ethyl caproylacetate, ethyl isocaproylacetate, ethyl heptanoylacetate, methyl phenylacetoacetate and methyl α-methylacetoacetate.

Among the foregoing there is used particularly preferably methyl acetoacetate, ethyl acetoacetate, isopropyl acetoacetate, butyl acetoacetate or ethyl pyruvate.

The above compounds can be used singly or in mixtures as the diketone compound having an alkoxy group.

Preferably, the content of the diketone compound having an alkoxy group is 0.02 to 2 as a molar ratio with respect to zinc in the dialkylzinc-containing solution or dialkylzinc partial hydrolysate, from the viewpoint of achieving a chemically stable dialkylzinc-containing solution or partial hydrolysate-containing solution. Preferably, the molar ratio with respect to zinc in the dialkyizinc-containing solution or dialkylzinc partial hydrolysate is 0.05 to 1.5, and yet more preferably 0.1 to 1.2. The upper limit can be set as appropriate for instance depending on the concentration of the dialkylzinc or dialkylzinc partial hydrolysate in the solution, and on the content and type of the solvent. By using the dialkylzinc in the form of a partial hydrolysate, chemical stability towards air is it proved as compared to that of the dialkylzinc; however, stability is still insufficient, and hence it is preferable to mix the dialkylzinc with a predetermined amount of a diketone compound having an alkoxy group, from the viewpoint of obtaining a chemically more stable partial hydrolysate-containing solution.

The method for incorporating the diketone compound having an alkoxy group into a dialkylzinc-containing solution or dialkylzinc hydrolysate containing solution may involve, in a case where a dialkylzinc-containing solution is used, for instance adding a diketone compound having an alkoxy group after mixing of the dialkylzinc and the solvent, or may involve adding the diketone compound having an alkoxy group to the solvent, followed by mixing with the dialkylzinc. In the case where a dialkylzinc hydrolysate-containing solution is used, the method may involve for instance mixing in the diketone compound having an alkoxy group, during preparation or after preparation of the dialkylzinc hydrolysate-containing solution.

The underlying reason for the enhanced stability in the air due to the use of the diketone compound having an alkoxy group is unclear. Without being bound by theory, it is estimated that the diketone compound having an alkoxy group elicits a significant improvement in stability towards air for instance on account of coordination bonds with zinc formed by unshared electron pairs of oxygen in the structure of the compound.

Other elements such as Mg, B, Al, Ga, In, Sn, Si, Ti, Zr and Ge may coexist in the solution of the present invention.

For instance, a zinc oxide thin film doped with Al, Ga or In can be obtained through film formation using a solution in which a group 13 element such a B, Al, Ga or In coexists. These doped zinc oxide thin films can be used, for instance, as transparent conductive films.

These elements can be added in the form of organic compounds or inorganic compounds. For instance in B, Al, Ga and In can be used in the form of an organic compound, for example an alkylated compound such as triethylaluminum, triethylgallium, trimethylgallium or trimethylindium; a carboxylate salt such as aluminum acetate, gallium acetate or indium acetate; an acetylacetonate salt such as aluminum acetylacetonate, gallium acetylacetonate or indium acetylacetonate; or an alkoxy compound such as aluminum triisopropoxide, gallium triethoxide or indium isopsopoxy, as well as an inorganic compound such as chlorides, nitrates and sulfates of the foregoing, and also mixtures of the foregoing.

[Method for Producing Zinc Oxide Thin Film]

A second aspect of the present invention is a method for producing a zinc oxide thin film, the method including coating a base material with a solution containing at least one of a dialkylzinc and a dialkylzinc partial hydrolysate of the present invention.

The base material can be coated with the above solution in accordance with a common method such as spin coating, dip coating, screen printing, bar coating, slit coating, die coating, gravure coating, roll coating, curtain coating, spray pyrolysis, electrostatic spray pyrolysis, inkjet and mist CVD.

The atmosphere in which the base material is coated with the solution is not particularly limited, and can be for instance an inert atmosphere or an air atmosphere. From the viewpoint of economy, coating is however preferably carried out in an air atmosphere, also in terms of convenience of equipment.

The humidity of the atmosphere in which the base material is coated with the solution is not particularly limited, and for instance coating may be carried out in an atmosphere at a relative humidity of 35% to 80%.

Coating of the base material with the solution can be performed under pressure or under reduced pressure, but herein it is preferable to utilize equipment in which coating is carried out under atmospheric pressure, in terms of economy.

The base material is not particularly limited, and may be for instance glass such as lead glass, soda glass, borosilicate glass or alkali-free glass; an oxide such as silica, alumina, titanic, zirconia or a complex oxide; a polymer such as polyethylene (PE), polypropylene (PP), polyethylene terephthalate (PET), polyethylene naphthalate (PEN), polymethyl methaclate (PMMA), polycarbonate (PC), polyphenylene sulfide (PPS), polystyrene (PS), polyvinyl alcohol (PVA), polyvinyl chloride (PVC), polyvinylidene chloride, a cyclic polyolefin (COP), an ethylene-vinyl acetate copolymer (EVA), a polyimide, a polyamide, a polyethersulfone (PES), a polyurethane, triacetate, triacetyl cellulose (TAC), cellophane, polytetrafluoroethylene (PTFE), polychlorotrifluoroethylene (PCTFE), polyvinylidene fluoride (PVDF), polyvinyl fluoride (PVF), a perfluoroalkoxy fluororesin (PFA), an tetrafluoroethylene-hexafluoropropylene copolymer (ETFE) or an ethylene-chlorotrifluoroethylene copolymer (ECTFE).

The shape of the base material is not particularly limited, and examples thereof include for instance powders, films, plates and three-dimensional structures having a three-dimensional shape.

The base material coated with a solution containing at least one of a dialkylzinc and a dialkylzinc partial hydrolysate of the present invention can be dried by evaporating the solvent at a predetermined temperature, and then baked at a predetermined temperature, or drying and baking can be performed in parallel at a predetermined temperature to form a zinc oxide thin film. In a case where coating is carried out by spray pyrolysis, electrostatic spray pyrolysis, inkjet or mist CVD, the base material can be heated to a predetermined temperature prior to coating. This makes it possible to dry the coating by evaporating the solvent, simultaneously with coating, or to perform baking simultaneously with drying.

The temperature for drying the solvent is preferably 300° C. or lower, and lies more preferably between 20° C. to 250° C., for instance with the heat resistance of the base material in mind. The solvent can be dried for instance over 0.5 to 60 minutes. The above ranges are however not meant to be limiting.

Baking for forming zinc oxide can be carried out at any temperature, for instance in the range of 50° C. to 550° C. Herein it is appropriate to set a temperature such that the base material is not damaged, taking into consideration the type (heat resistance) of the base material From the viewpoint of forming a zinc oxide thin film so as to preclude damage to the base material, also in base materials having a low heat resistance, in the method of the present invention it is appropriate to form the zinc oxide thin film by baking a coating film of the dialkylzinc partial hydrolysate-containing solution at a temperature of 300° C. or lower. Baking can be carried out in parallel with solvent drying in a case where the predetermined temperature for baking is identical to the predetermined temperature for solvent diving. Regarding baking time, baking can be performed for instance over 0.5 to 300 minutes, both in a case of baking at a different temperature after a precursor film has been obtained through solvent drying, and in a case where solvent drying and baking are carried out in parallel. The baking time can be set as appropriate depending for instance on the baking temperature, the solution that contains at least one of a dialkylzinc and a dialkylzinc partial hydrolysate, and the thickness of the coating film, The thickness of the zinc oxide thin film thus obtained can be for instance of 0.005 to 3 μm. The thickness of the zinc oxide thin film being formed in a single operation can be adjusted through adjustment of the composition and/or concentration of the solution containing at least one of a dialkylzinc and a dialkylzinc partial hydrolysate, and adjustment of the coating method and conditions. A thicker film can be obtained by repeating as needed, a plurality of times, the above coating, drying and baking steps.

The crystallinity and denseness of zinc oxide can be increased as needed by heating, at a predetermined temperature, the zinc oxide thin film obtained as described above, in an oxidizing gas atmosphere of oxygen or the like, a reducing gas atmosphere of hydrogen or the like, a water vapor atmosphere in which a large amount of moisture is present, or a plasma atmosphere of for instance argon, nitrogen or oxygen. Residual organic matter or the like in the zinc oxide thin film that is obtained can be removed through irradiation of for instance ultraviolet rays, or as a result of a microwave treatment.

EXAMPLES

The present invention will be explained next in further detail based on examples. The examples are however illustrative of the invention, which is not meant to be limited to the examples.

A solution containing at least one of a dialkylzinc and a dialkylzinc partial hydrolysate of the present invention was prepared in a nitrogen gas atmosphere. All the solvents used had been dehydrated and degassed.

<Measurement of Physical Properties>

Each dialkylzinc-containing solution or dialkylzinc partial hydrolysate-containing solution of the present invention was dissolved in $C_6D_6$, and thereafter a 1H-NMR measurement was performed using an NMR apparatus ("JNM-ECA500" by JEOL RESONANCE Inc.).

Each zinc oxide thin film produced in accordance with the production method of the present invention was subjected to IR measurement in a relative manner, without ATR correction by ATR (Attenuated Total Reflection), using an ZnSe prism, in an FT-IR spectrometer ("FT/IR-4100" by JASCO Corporation).

Thin films with refractive index in excess of 1.7 are difficult to measure when using a conventional ZnSe prism, and it was inferred that measurement would be likewise difficult given that the refractive index of ordinary zinc oxide is 1.9. Surprisingly, the measurements could nevertheless be carried out.

The thickness of the zinc oxide thin films produced in accordance with the production method of the present invention was measured using a stylus profilometer (Dektak XT-S, by Bruker Corporation), upon scraping of part of the film with a knife.

The homogeneity (occurrence or absence of cracks or peeling) of each zinc oxide thin film was evaluated as follows (Tables 2 and 3) by visually checking the occurrence or absence of cracks or peeling using an optical microscope.

A . . . No cracks or peeling observed in the thin film.
B . . . Peeling absent in the thin film, but with slight observable cracking.
C . . . For instance conspicuously observable cracking and/or peeling in the thin film.

Reference Example 1

A mixture resulting from mixing 360.02 g of 1,2-diethoxyethane and 40 g of diethylzinc at room temperature was cooled down to −11° C., and then 28.5 g of a 12.3 mass % water-containing THF solution ([water]/[diethylzinc]=0.6) was added dropwise over 3.5 hours, under stirring. After 40 minutes of aging at −10° C., an aging reaction was carried out through continued stirring overnight, while the whole warmed up to 25° C., to yield a pale-yellow transparent 1,2-diethoxyethane solution (Composition A) of a diethylzinc partial hydrolysate composition.

Reference Example 2

Herein a mixture resulting from mixing 15.0 g of toluene and 0.91 g of triethylgallium at room temperature was cooled down to −8° C., and then 3.6 g of a 2.8 mass % water-containing THF solution was added dropwise thereonto over 15 minutes, under stirring. Then a mixture of 283 g of toluene and 36 g of diethylzinc was added over 2 hours, in a cooled state, to the obtained reaction mixture. Once dropwise addition was over, the whole was stirred for 30 minutes, after which 36 g of an 8.3 mass % water-containing THF solution ([water]/[diethylzinc]=0.6) cooled to −10° C. was added dropwise to the reaction mixture over 5.4 hours. After 30 minutes of aging at −10° C., an aging reaction was carried out through continued stirring overnight, while the whole warmed up to 25° C., to yield a pale-yellow transparent toluene solution (Composition B) of a diethylzinc partial hydrolysate composition.

Reference Example 3

A mixture resulting from mixing 30.0 g of 1,2-diethoxyethane and 1.02 g of triethylgallium at room temperature was cooled down to −11° C., and then 5.12 g of a 2.34 mass % water-containing THF solution was added dropwise thereonto over 10 minutes, under stirring. Then a mixture of 325 g of 1,2-diethoxyethane and 40 g of diethylzinc was added over 4.4 hours, in a cooled state, to the obtained reaction mixture. Once dropwise addition was over, the whole was stirred for 10 minutes, after which 28.4 g of a 11.2 mass % water-containing THF solution ([water]/[diethylzinc]=0.6) cooled to −10° C. was added dropwise to the reaction mixture over 1.25 hours. After 30 minutes of aging at −10° C., an aging reaction was carried out through continued stirring overnight, while the whole warmed up to 25° C., to yield a colorless transparent 1,2-diethoxyethane solution (Composition C) of a diethylzinc partial hydrolysate composition.

Reference Example 4

Herein a mixture resulting from mixing 20.0 g of xylene and 2.03 g of triethylgallium at room temperature was cooled down to −11° C., and then 3.23 g of a 7.2 mass % water-containing THF solution was added dropwise thereonto over 10 minutes, under stirring. Then a mixture of 420 g of xylene and 80 g of diethylzinc was added in a cooled state to the obtained reaction mixture over 3 hours. Once dropwise addition was over, the whole was stirred for 26 minutes, after which 66.77 g of a 10.1 mass % water-containing THF solution ([water]/[diethylzinc]=0.6) cooled to −13° C. was added dropwise to the reaction mixture over 3.4 hours. After 15 minutes of aging at −12° C., an aging reaction was carried out through continued stirring overnight, while the whole warmed up to 25° C. A very small amount of cloudiness in the solution obtained after aging was filtered off, to yield a pale-yellow transparent xylene solution (Composition D) of a diethylzinc partial hydrolysate composition.

Reference Example 5

A mixture resulting from mixing 204.56 g of N-methyl-2-pyrrolidone (hereafter NMP) and 22.73 g of diethylzinc at room temperature was cooled down to −11° C., and then 17.49 g of a 11.4 mass % water-containing NMP solution was added dropwise over 1.7 hours, under stirring. After 30 minutes of aging at −10° C., 1.17 g of a 12.8 mass % water-containing NMP solution were further added dropwise under stirring over 1 hour ([water]/[diethylzinc]=0.65 (molar ratio), as the total of the addition amounts of water). An aging reaction was carried out through continued stirring overnight, while the whole warmed up to 25° C., to yield a colorless transparent 1,2-diethoxyethane solution (Composition E) of a diethylzinc partial hydrolysate composition.

Examples 1 to 20

A diketone compound having an alkoxy group was then added in the quantitative ratios given in Table 1, in a nitrogen atmosphere, to each dialkylzinc partial hydrolysate-containing solution of Reference examples 1 to 5, with mixing at room temperature, to thereby prepare solutions of the present invention (Compositions 1 to 20).

Further, Compositions A to E in Reference examples 1 to 5 were divided each into 25 g aliquots in order to evaluate formation of a zinc oxide thin film.

TABLE 1

|  | Composition of the invention | Diethylzinc partial hydrolysate composition | Quantity g |
|---|---|---|---|
| Example 1 | Composition 1 | Composition A | 17.71 |
| Example 2 | Composition 2 | Composition B | 20.03 |
| Example 3 | Composition 3 | Composition B | 35.00 |
| Example 4 | Composition 4 | Composition B | 27.26 |
| Example 5 | Composition 5 | Composition B | 27.27 |
| Example 6 | Composition 6 | Composition C | 27.33 |
| Example 7 | Composition 7 | Composition D | 26.630 |
| Example 8 | Composition 8 | Composition E | 22.40 |
| Example 9 | Composition 9 | Composition B | 198.60 |
| Example 10 | Composition 10 | Composition B | 20.31 |
| Example 11 | Composition 11 | Composition B | 19.79 |
| Example 12 | Composition 12 | Composition B | 20.01 |
| Example 13 | Composition 13 | Composition B | 19.56 |
| Example 14 | Composition 14 | Composition B | 19.52 |
| Example 15 | Composition 15 | Composition B | 20.00 |
| Example 16 | Composition 16 | Composition B | 20.00 |
| Example 17 | Composition 17 | Composition B | 20.00 |
| Example 18 | Composition 18 | Composition B | 20.00 |
| Example 19 | Composition 19 | Composition B | 20.00 |
| Example 20 | Composition 20 | Composition B | 20.00 |
| Reference example 1 |  | Composition A | 25.00 |
| Reference example 2 |  | Composition B | 25.00 |
| Reference example 3 |  | Composition C | 25.00 |
| Reference example 4 |  | Composition D | 25.00 |
| Reference example 5 |  | Composition E | 25.00 |

|  | Diketone compound having an alkoxy group | Quantity g | Additive/Zn (molar ratio) |
|---|---|---|---|
| Example 1 | Ethyl acetoacetate | 0.192 | 0.10 |
| Example 2 | Ethyl acetoacetate | 2.030 | 1.00 |
| Example 3 | Ethyl acetoacetate | 0.350 | 0.10 |
| Example 4 | Ethyl acetoacetate | 0.140 | 0.05 |
| Example 5 | Ethyl acetoacetate | 0.060 | 0.02 |

TABLE 1-continued

| Example 6 | Ethyl acetoacetate | 0.270 | 0.10 |
| Example 7 | Ethyl acetoacetate | 0.380 | 0.10 |
| Example 8 | Ethyl acetoacetate | 0.240 | 0.10 |
| Example 9 | Ethyl acetoacetate | 2.060 | 0.10 |
| Example 10 | Methyl acetoacetate | 1.840 | 1.00 |
| Example 11 | Isopropyl acetoacetate | 2.220 | 1.00 |
| Example 12 | Butyl acetoacetate | 2.460 | 1.00 |
| Example 13 | sec-butyl acetoacetate | 2.410 | 1.00 |
| Example 14 | tert-butyl acetoacetate | 2.400 | 1.00 |
| Example 15 | Methyl acetoacetate | 0.180 | 0.10 |
| Example 16 | Isopropyl acetoacetate | 0.220 | 0.10 |
| Example 17 | Butyl acetoacetate | 0.250 | 0.10 |
| Example 18 | sec-butyl acetoacetate | 0.250 | 0.10 |
| Example 19 | tert-butyl acetoacetate | 0.250 | 0.10 |
| Example 20 | Ethyl pyruvate | 1.810 | 1.00 |
| Reference example 1 | None | 0 | 0 |
| Reference example 2 | None | 0 | 0 |
| Reference example 3 | None | 0 | 0 |
| Reference example 4 | None | 0 | 0 |
| Reference example 5 | None | 0 | 0 |

Example 21

Figure 1:
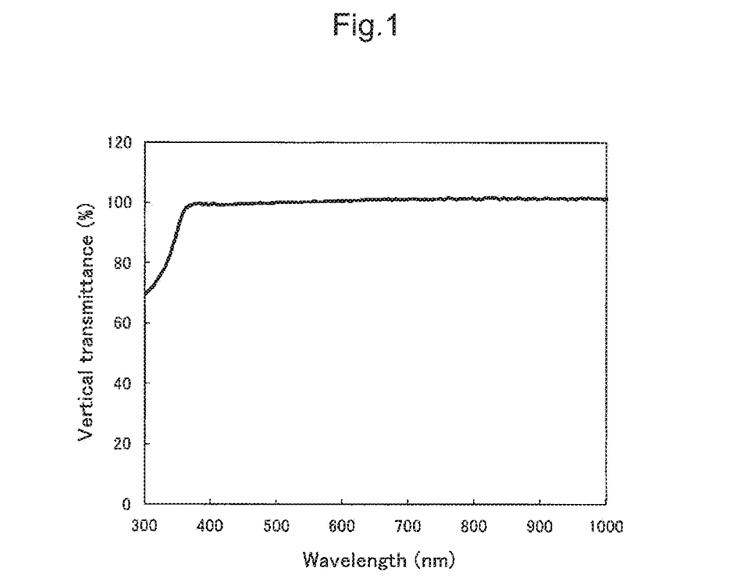
FIG. 1 is a vertical transmittance spectrum of a zinc oxide thin film obtained in Example 21.

Herein 50 til of the composition of Example 1 (Composition 1) resulting from adding ethyl acetoacetate to the 1,2-diethoxyethane solution (Composition A) of a diethylzinc partial hydrolysate composition were added dropwise onto a 15 mm square glass substrate (Eagle XG, by Corning Incorporated), in a moist air atmosphere (humidity: 65%) at room temperature (temperature: 23° C.), and the glass substrate was coated with the composition through spinning for 20 seconds at 1000 rpm, using a spin coater. A thin film was then formed by heating with drying for 2 minutes at 100° C. The vertical transmittance of the obtained zinc oxide thin film was measured. The resulting spectrum is illustrated in FIG. 1. Vertical transmittance towards 550 nm light in the obtained thin film was 99%. Formation of zinc oxide was confirmed on the basis of the low vertical transmittance in the ultraviolet region. No peeling, cracking or the like was observed in the film. The thickness of the obtained thin film was 90 nm.

Figure 2:
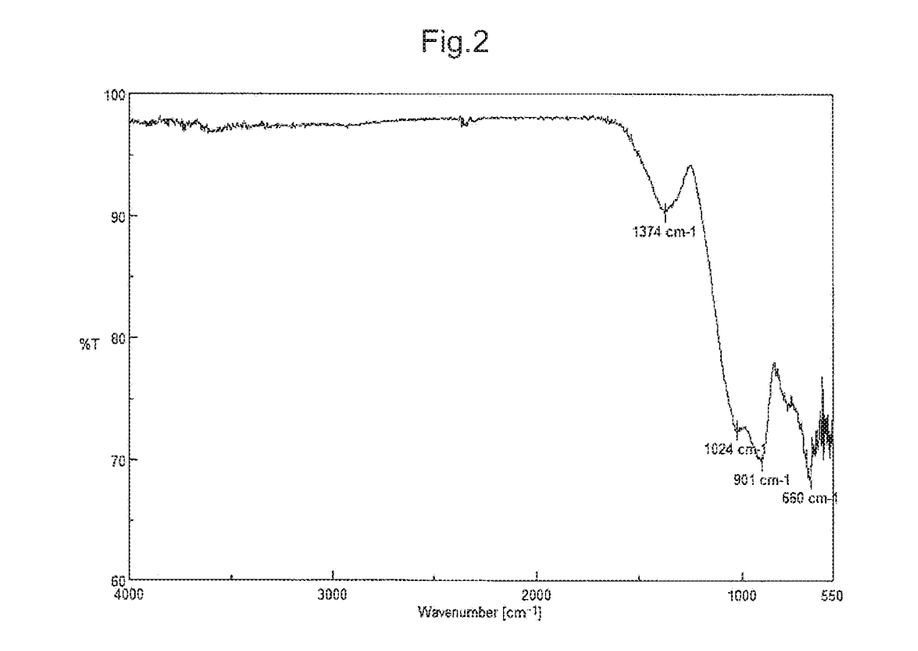
FIG. 2 is an IR spectrum, by ATR, of the zinc oxide thin film obtained in Example 21.

A spectrum such as the one illustrated in FIG. 2 was obtained in an IR measurement by ATR. Broad Zn—O—Zn vibration peaks were observed approximately from 550 to 1500 $cm^{-1}$, which revealed the formation of Zn—O—Zn. Formation of a zinc oxide thin film was therefore confirmed. There were virtually no vibration peaks of organic matter around 3000 $cm^{-1}$, which indicated that little residual organic matter had remained.

Comparative Example 1

A thin film was formed in the same way as in Example 1, but herein there was used only the 1,2-diethoxyethane solution (Composition A) of the diethylzinc partial hydrolysate composition obtained in Reference example 1. A measurement of vertical transmittance yielded a vertical transmittance of 65% towards 550 nm light, indicative of an opaque film at less than 80%. Peeling in the as observable, and adhesion of the film to a substrate was poor.

Examples 22 to 27

Composition 1 obtained in Example 1, Composition 7 obtained in Example 7, Composition 6 obtained in Example 6 and Composition 8 obtained in Example 8 were each coated onto substrates, in accordance with the method described in Example 21, and each substrate was heated and simultaneously dried at 100° C. or 500° C. for 2 minutes, to thereby form a thin film. As regards relative humidity at the time of film formation, all the obtained zinc oxide thin films were transparent thin films at 90% or higher, with no peeling, cracking or the like being observed in any of the films.

Comparative Examples 2 to 6

Composition A obtained in Reference example 1, Composition D obtained in Reference example 4 and Composition C obtained in Reference example 3 were each coated onto substrates, in accordance with the method described in Example 21, and each substrate was heated and simultaneously dried at 100° C. or 500° C. for 2 minutes, to thereby form a thin film. The zinc oxide thin films formed at 100° C. all exhibited visible peeling. The zinc oxide thin films formed at 500° C. exhibited visible peeling, and were all opaque thin films at less than 80%.

Examples 28 to 35

Compositions 2 to 5 obtained in Examples 2 to 5 and in which Composition B and ethyl acetoacetate at different concentrations coexisted, were each coated onto substrates in accordance with the method described in Example 21, and each substrate was heated and simultaneously dried at 100° C. or 500° C. for 2 minutes, to thereby form a thin film. The obtained zinc oxide thin films were all transparent thin films at 90% or higher. For instance, no peeling or cracking was observed in compositions with a molar ratio of 0.1 or higher of diketone compound having an alkoxy group with respect to zinc. Compositions where the above molar ratio was 0.05 or 0.02 exhibited slight observable cracking, but no pronounced peeling or the like was observed.

Comparative Examples 7 and 8

Only the Composition B obtained in Reference example 2 was each coated onto substrates, in accordance with the method described in Example 21, and each substrate was heated and simultaneously dried at 100° C. or 500° C. for 2 minutes, to thereby form a thin film. The zinc oxide thin films formed at 100° C. or 500° C. all exhibited peeling, and all were opaque thin films at less than 80%.

Examples 36 and 37

Composition 20 obtained in Example 20 was each coated onto substrates, in accordance with the method described in Example 21, and each substrate was heated and simultaneously dried at 100° C. or 500° C. for 2 minutes, to thereby form a thin film. The obtained zinc oxide thin films were all transparent thin films at 95% or higher. For instance, no peeling or cracking was observed in compositions with a molar ratio of 0.1 or higher of diketone compound having an alkoxy group with respect to zinc.

Examples 38 to 56

Compositions 10 to 19 of Examples 10 to 19, obtained by addition sf various types of diketone compound having an alkoxy group to Composition B, were each coated onto substrates, in accordance with the method described in Example 21, and each substrate was heated and simultaneously dried at 100° C. or 500° C. for 2 minutes, to thereby form a thin film. The obtained zinc oxide thin films were all transparent thin films at 90% or higher. No peeling, crack or the like was observed in the obtained zinc oxide thin films.

Example 57

Herein 155.72 g of toluene, 17.30 g of diethylzinc, 0.44 g of triethylgallium and 0.59 g of ethyl acetoacetate were mixed at room temperature, to prepare a toluene solution (Composition F) containing diethylzinc and that contained a diketone compound having an alkoxy group.

This Composition F was sprayed for 32 minutes at 1 mL/minute onto a substrate heated at 200° C., to form a sprayed film in the atmosphere. The relative humidity at the time of film formation was 73% to 75%.

Figure 3:
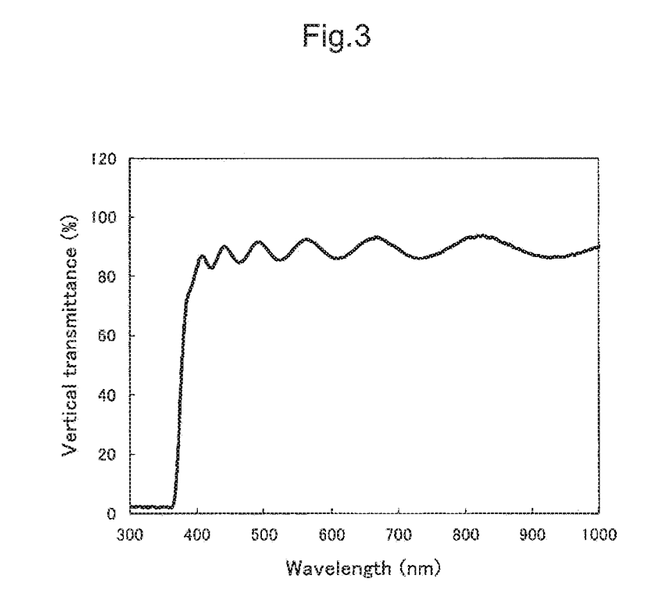
FIG. 3 is a vertical transmittance spectrum of a zinc oxide thin film obtained in Example 57.
Figure 4:
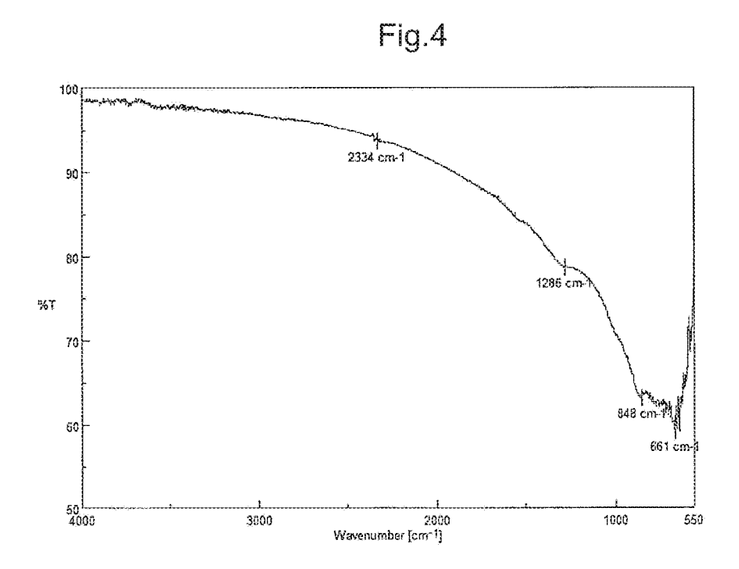
FIG. 4 is an IR spectrum, by ATR, of the zinc oxide thin film obtained in Example 57.

The vertical transmittance of the obtained zinc oxide thin film was measured, A spectrum such as the one in FIG. 3 was obtained; vertical transmittance towards 550 nm light was herein 91%. Formation of zinc oxide was confirmed on the basis of the low vertical transmittance in the ultraviolet region. A spectrum such as the one illustrated in FIG. 4 was obtained in an IR measurement by ATR. Broad Zn—O—Zn vibration peaks were observed approximately from 550 to 1500 $cm^{-1}$, which revealed the formation of Zn—O—Zn. Formation of a zinc oxide thin film was therefore confirmed. There were virtually no vibration peaks of organic matter around 3000 $cm^{-1}$, which indicated that little residual organic matter had remained. The thickness of the obtained thin film was 821 nm. The resistance of the thin film was lowered to 1080 Ω/square through the use of UV having a wavelength of 254 nm for 5 minutes.

Example 58

A toluene solution (Composition G) containing diethylzinc and that contained a diketone compound having an alkoxy group was prepared in accordance with the same method as in Example 57, but without incorporating herein the triethylgallium of Example 57.

This Composition F was sprayed for 32 minutes at 1 mL/minute onto a substrate heated at 200° C., to form a sprayed film in the atmosphere. Relative humidity at the time of film formation was 73% to 75%.

The vertical transmittance of the obtained zinc oxide thin film was measured in the same way as in Example 57, vertical transmittance towards 550 nm light was 92%, and vertical transmittance in the ultraviolet region was low. The thin film obtained in the same way as in Example 57 was subjected to an IR measurement by ATR, which revealed the formation of Zn—O—Zn. From the above it was thus found that a zinc oxide thin film was formed as a result of the operation in Example 57. There were virtually no vibration peaks of organic matter around 3000 $cm^{-1}$, which indicated that little residual organic matter had remained.

TABLE 2

|  | Composition of the invention | Diketone compound having an alkoxy group | Molar ratio of diketone compound having an alkoxy group with respect to zinc |
|---|---|---|---|
| Example 21 | Composition 1 | Ethyl acetoacetate | 0.1 |
| Example 22 | Composition 1 | Ethyl acetoacetate | 0.1 |
| Example 23 | Composition 7 | Ethyl acetoacetate | 0.1 |
| Example 24 | Composition 7 | Ethyl acetoacetate | 0.1 |
| Example 25 | Composition 6 | Ethyl acetoacetate | 0.1 |
| Example 26 | Composition 6 | Ethyl acetoacetate | 0.1 |
| Example 27 | Composition 8 | Ethyl acetoacetate | 0.1 |
| Comparative example 1 | Composition A | None | 0 |
| Comparative example 2 | Composition A | None | 0 |
| Comparative example 3 | Composition D | None | 0 |
| Comparative example 4 | Composition D | None | 0 |
| Comparative example 5 | Composition C | None | 0 |
| Comparative example 6 | Composition C | None | 0 |
| Example 28 | Composition 2 | Ethyl acetoacetate | 1 |
| Example 29 | Composition 3 | Ethyl acetoacetate | 0.1 |
| Example 30 | Composition 4 | Ethyl acetoacetate | 0.05 |
| Example 31 | Composition 5 | Ethyl acetoacetate | 0.02 |
| Comparative example 7 | Composition B | None | 0 |
| Example 32 | Composition 2 | Ethyl acetoacetate | 1 |
| Example 33 | Composition 3 | Ethyl acetoacetate | 0.1 |
| Example 34 | Composition 4 | Ethyl acetoacetate | 0.05 |
| Example 35 | Composition 5 | Ethyl acetoacetate | 0.02 |
| Comparative example 8 | Composition B | None | 0 |

TABLE 2-continued

| | Substrate heating temperature (° C.) | Relative humidity (%) in coating atmosphere | Cracking/ peeling | Transmittance (%) |
|---|---|---|---|---|
| Example 21 | 100 | 57 | A | 99 |
| Example 22 | 500 | 65 | A | 99 |
| Example 23 | 100 | 48 | A | 99 |
| Example 24 | 500 | 45 | A | 99 |
| Example 25 | 100 | 40 | A | 99 |
| Example 26 | 500 | 39 | A | 96 |
| Example 27 | 100 | 67 | A | 99 |
| Comparative example 1 | 100 | 59 | C | 65 |
| Comparative example 2 | 500 | 65 | C | 89 |
| Comparative example 3 | 100 | 47 | C | 70 |
| Comparative example 4 | 500 | 45 | C | 71 |
| Comparative example 5 | 100 | 67 | C | 86 |
| Comparative example 6 | 500 | 57 | C | 68 |
| Example 28 | 100 | 50 | A | 99 |
| Example 29 | 100 | 51 | A | 99 |
| Example 30 | 100 | 52 | A | 99 |
| Example 31 | 100 | 50 | B | 95 |
| Comparative example 7 | 100 | 46 | C | 58 |
| Example 32 | 500 | 47 | A | 98 |
| Example 33 | 500 | 46 | A | 98 |
| Example 34 | 500 | 47 | B | 98 |
| Example 35 | 500 | 52 | B | 95 |
| Comparative example 8 | 500 | 50 | C | 64 |

TABLE 3

| | Composition of the invention | Diketone compound having an alkoxy group | Molar ratio of diketone compound having an alkoxy group with respect to zinc |
|---|---|---|---|
| Example 36 | Composition 20 | Ethyl pyruvate | 1 |
| Example 37 | Composition 20 | Ethyl pyruvate | 1 |
| Example 38 | Composition 10 | Methyl acetoacetate | 1 |
| Example 39 | Composition 11 | Isopropyl acetoacetate | 1 |
| Example 40 | Composition 12 | Butyl acetoacetate | 1 |
| Example 41 | Composition 13 | sec-butyl acetoacetate | 1 |
| Example 42 | Composition 14 | tert-butyl acetoacetate | 1 |
| Example 43 | Composition 10 | Methyl acetoacetate | 1 |
| Example 44 | Composition 11 | Isopropyl acetoacetate | 1 |
| Example 45 | Composition 12 | Butyl acetoacetate | 1 |
| Example 46 | Composition 13 | sec-butyl acetoacetate | 1 |
| Example 47 | Composition 14 | tert-butyl acetoacetate | 1 |
| Example 48 | Composition 15 | Methyl acetoacetate | 0.1 |
| Example 49 | Composition 16 | Isopropyl acetoacetate | 0.1 |
| Example 50 | Composition 17 | Butyl acetoacetate | 0.1 |
| Example 51 | Composition 18 | sec-butyl acetoacetate | 0.1 |
| Example 52 | Composition 19 | tert-butyl acetoacetate | 0.1 |
| Example 53 | Composition 16 | Isopropyl acetoacetate | 0.1 |
| Example 54 | Composition 17 | Butyl acetoacetate | 0.1 |
| Example 55 | Composition 18 | sec-butyl acetoacetate | 0.1 |
| Example 56 | Composition 19 | tert-butyl acetoacetate | 0.1 |

| | Substrate heating temperature (° C.) | Relative humidity (%) in coating atmosphere | Cracking/ peeling | Transmittance (%) |
|---|---|---|---|---|
| Example 36 | 100 | 62 | A | 99 |
| Example 37 | 500 | 55 | A | 98 |
| Example 38 | 100 | 72 | A | 94 |
| Example 39 | 100 | 72 | A | 99 |
| Example 40 | 100 | 72 | A | 94 |
| Example 41 | 100 | 72 | A | 99 |
| Example 42 | 100 | 71 | A | 99 |
| Example 43 | 500 | 62 | A | 94 |
| Example 44 | 500 | 61 | A | 99 |
| Example 45 | 500 | 59 | A | 98 |
| Example 46 | 500 | 58 | A | 98 |
| Example 47 | 500 | 58 | A | 98 |
| Example 48 | 100 | 64 | A | 98 |
| Example 49 | 100 | 64 | A | 99 |
| Example 50 | 100 | 64 | A | 99 |

TABLE 3-continued

| Example 51 | 100 | 63 | A | 99 |
| Example 52 | 100 | 63 | A | 99 |
| Example 53 | 500 | 58 | A | 99 |
| Example 54 | 500 | 56 | A | 99 |
| Example 55 | 500 | 55 | A | 99 |
| Example 56 | 500 | 54 | A | 98 |

INDUSTRIAL APPLICABILITY

The present invention is useful in the field of production of the zinc oxide thin films. Zinc oxide thin films include for instance photocatalyst films, UV cutting films, infrared reflection films, CIGS, buffer layers of organic thin-film solar cells, electrode films of dye sensitized solar cells, antistatic films, thin-film transistors, compound semiconductor light-emitting elements, phosphor elements, antibacterial/deodorant films, piezoelectric films, varistor films and plating films.

The invention claimed is:

1. A solution consisting essentially of a diketone compound having an alkoxy group, a dialkylzinc represented by formula (1) below and/or a partial hydrolysate of the dialkylzinc, and a solvent, wherein the solvent is at least one solvent selected from the group consisting of aliphatic hydrocarbons, alicyclic hydrocarbons, aromatic hydrocarbons, hydrocarbon solvents, ether compounds, linear amide compounds and cyclic amide compounds, a molar ratio of the diketone compound having an alkoxy group contained in the solution to zinc in the dialkylzinc or the partial hydrolysate of the dialkylzinc is 0.01 to 2, $$ZnR^{10}_2 \quad (1)$$

wherein in the formula (1), $R^{10}$ is a $C_1$-$C_6$ linear or branched alkyl group.

2. The solution according to claim 1, wherein the diketone compound having an alkoxy group is one or two or more diketone compounds selected from the group consisting of an α-diketone compound having an alkoxy group, a β-diketone compound having an alkoxy group, an α-keto ester and a β-keto ester.

3. The solution according to claim 1, wherein the diketone compound having an alkoxy group is a compound represented by formula (2) or formula (3), or a mixture thereof, (2)

wherein in the formula (2), $R_1$ represents a substituent selected from the group consisting of $C_1$-$C_6$ alkyl groups, phenyl groups, and benzyl groups, and $R_2$ represents a $C_1$-$C_6$ alkyl group, (3)

and wherein in the formula (3), $R_1$ represents a substituent selected from the group consisting of $C_1$-$C_6$ alkyl groups, phenyl groups and benzyl groups; $R_2$ represents a $C_1$-$C_6$ alkyl group; and $R_3$ and $R_4$ each represent hydrogen or a $C_1$-$C_6$ alkyl group.

4. The solution according to claim 1, wherein the diketone compound having an alkoxy group is methyl acetoacetate, ethyl acetoacetate, isopropyl acetoacetate, butyl acetoacetate and ethyl pyruvate, or a mixture thereof.

5. The solution according to claim 1, wherein the dialkylzinc is diethylzinc.

6. The solution according to claim 1, wherein the partial hydrolysate of the dialkylzinc is a partial hydrolysate resulting from hydrolysis with water at a molar ratio in the range of 0.4 to 0.9 with respect to zinc in the dialkylzinc.

7. The solution according to claim 1, wherein the partial hydrolysate of the dialkylzinc is a partial hydrolysate represented by formula (4) below, $$R^{10}\text{—Zn—}[O\text{—Zn}]_m\text{—}R^{10} \quad (4)$$

wherein in the formula (4), $R^{10}$ is a $C_1$-$C_6$ linear or branched alkyl group, and m is an integer from 1 to 20.

8. A method for producing a zinc oxide thin film, including a step of coating a base material with the solution according to claim 1.

9. The production method according to claim 8, including a step of heating the base material.

10. The production method according to claim 8, wherein the base material is coated with the solution in a state where the base material is heated to a temperature of 500° C. or lower.

11. The production method according to claim 8, wherein the coating is performed in the air.

12. The production method according to claim 8, wherein the coating is performed in an atmosphere having a relative humidity of 35% to 80%.

13. The production method according to claim 8, wherein the zinc oxide thin film has a transmittance equal to or higher than 80% to visible light of 550 nm.

* * * * *